Figure 1:
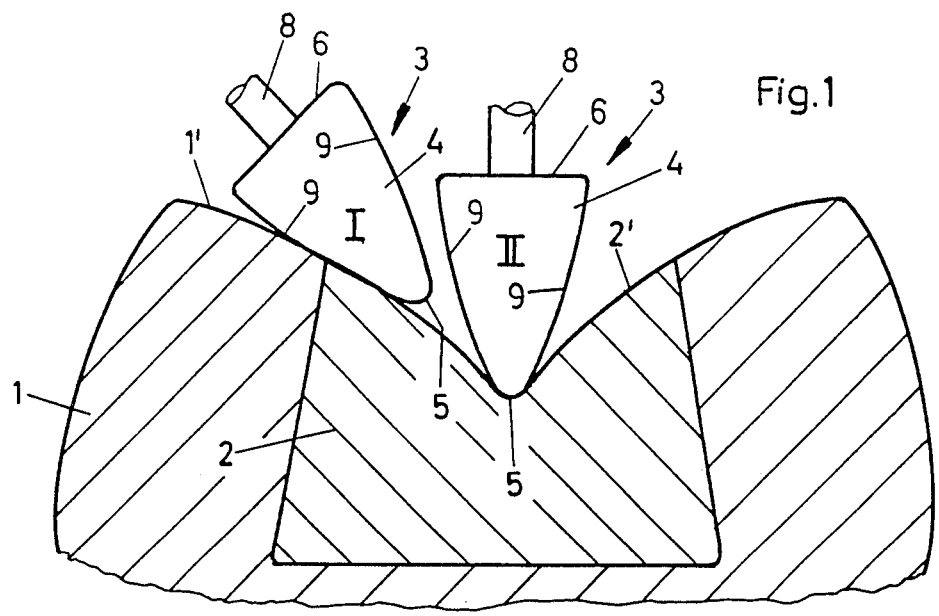

United States Patent [19]

Neumeyer

[11] Patent Number: 4,613,307
[45] Date of Patent: Sep. 23, 1986

[54] DENTAL TOOL

[76] Inventor: Stefan Neumeyer, Leminger Strasse 10, 8491 Eschikam, Fed. Rep. of Germany

[21] Appl. No.: 656,692

[22] Filed: Oct. 1, 1984

[30] Foreign Application Priority Data

Oct. 1, 1983 [DE] Fed. Rep. of Germany ....... 3335797
Oct. 21, 1983 [DE] Fed. Rep. of Germany ....... 3338256
Dec. 29, 1983 [DE] Fed. Rep. of Germany ....... 3347428

[51] Int. Cl.$^4$ .............................................. A61C 3/06
[52] U.S. Cl. .................................................... 433/166
[58] Field of Search ................................ 433/166, 141

[56] References Cited

U.S. PATENT DOCUMENTS 732,949 7/1903 Koenig .............................. 433/166
4,447,208 5/1984 Kawai ............................... 433/166

OTHER PUBLICATIONS

Veratex Convention Dental Catalogue Feb. 1976, p. 31.

Primary Examiner—Robert Peshock
Attorney, Agent, or Firm—Jacobs & Jacobs

[57] ABSTRACT

This invention refers to a finisher comprising a rotation-symmetrical, conical body with a plurality of cutting edges at the generated surface of this body as well a stem extending from the base of this body, the axis of which stem is coaxial with the axis of symmetry of the conical body. Alternatively, the invention refers to a dental grinding and/or polishing tool comprising of a rotation-symmetrical, conical body with a generated surface formed as a grinding or polishing surface as well a stem extending from the base.

5 Claims, 3 Drawing Figures

DENTAL TOOL

This invention refers to dental tools, namely to finishers comprising a rotation-symmetrical, conical body with a plurality of cutting edges at the surface of this body, and also comprising a stem extending from the base of this conical body the axis of which stem is arranged coaxial with the symmetrical axis of the conical body, as well to grinding and polishing tools comprising a rotation-symmetrical, conical body with a generated surface formed as a grinding and/or polishing surface, and also comprising a stem extending from the base of this conical body the axis of which stem is arranged coaxial with the symmetrical axis of the conical body.

Finishers are known in various embodiments and are used by the dentist f.e. to polish or finish the surface of tooth fillings (amalgam fillings, gold fillings or gold deposits, etc.) subsequent to coarsely completing said tooth fillings by means of a material removing step, and/or levelling (finishing the filling transitions) for obtaining a continuous transition between filling and adjacent tooth surface, and/or forming or alternatively modulating (finishing the fissures) according to the natural shape of a tooth at the treated position. Furthermore, finishers f.e. also are used to remove excessive filling material. Furthermore, finishers are used in making crowns, in recontouring in general as well in various grinding techniques.

Finishers according to the state of the art above all have the disadvantage that in general a number of finishers different in shape are necessary, which in view of their shape merely can be used for one predetermined operation step of an entire operation procedure or an entire finishing process, and are to be used one after the other until the treatment or finishing operation has been completed, which requires a time consuming change on the dental instrument (esp. elbow head).

Grinding and/or polishing tools for dental purposes are known per se in various embodiments and are used by the dentist for most different grinding and polishing steps. Grinding and/or polishing tools according to the state of the art above all have the disadvantage that in general a number of differently shaped tools are necessary, which in view of their shape merely can be used for one predetermined operation step of an entire operation procedure, and are to be used one after the other until the treatment or finishing operation has been completed, which requires a time-consuming change on the dental instrument (especially elbow head).

The problem to be overcome by this invention is to provide finishers and grinding and/or polishing tools, which in view of their unique shape can be used for the most different operation steps and, therefore, are universally useable.

For solving this problem finishers and grinding and/or polishing tools, of the above-described type according to this invention are formed in such a manner that the conical body is rounded at its tip, and that the operated surface of the conical body is curved in a convex manner in the direction of the basis to the tip (surface line = generatrix).

In view of this special shape the dental tool according to this application can be used for all operation steps, which usually are required, whereby the shape of the conical body according to this invention in view of the usual structure of dental instruments (especially elbow heads) with the various operation steps also allows the dentist to work correctly within the mouth of a patient, especially without any danger that during operation the finisher or the grinding and/or polishing tool or alternatively its tip will come close to the position of the patient's tongue or into the position of other devices or instruments (f.e. suction canule) arranged with the patient's mouth.

With one embodiment of the invention, which embodiment combines the requirement for universal versatility with the requirement for simple handling by the dentist, the conical body has a shape according to which the diameter or alternatively cross section of the conical body varies dependent on the distance from the base as follows:

| Distance from the base | Diameter |
| --- | --- |
| 0 units | 1,5 until 1,7 units |
| 1 unit | 1,3 until 1,45 units |
| 2 units | 1,0 until 1,2 units |
| 3 units | 0,5 until 0,7 units. |

If a less rounded tip will be required, the conical body has a shape, with which the last value of the above table is altered as follows:

| 3 units | 0,4 until 0,5 units |
| --- | --- |

The length of the conical body (distance between base and tip) is about 35 units, whereby one unit preferably corresponds to 10 mm.

Figure 2:
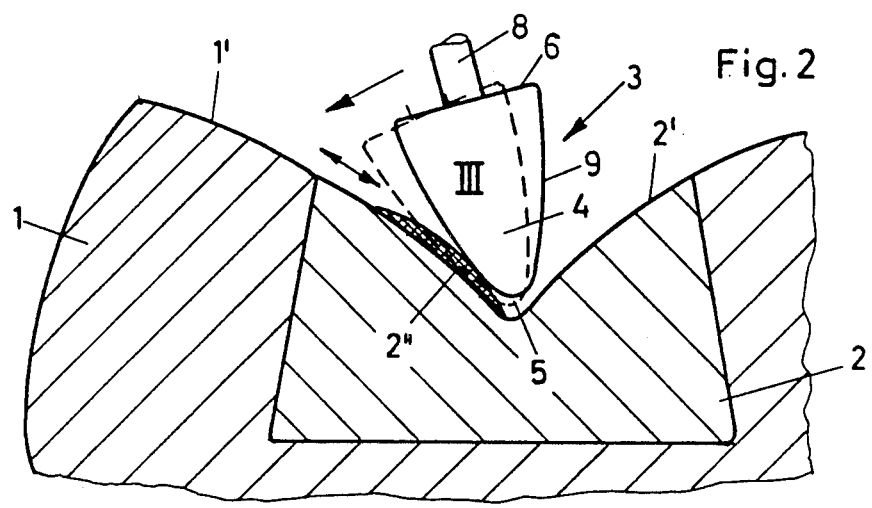
Figure 3:
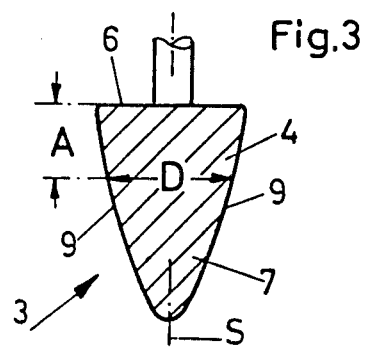

A special embodiment of the invention will now be described by way of example with reference to the accompaning drawings of which FIG. 1 shows a cross-section through a tooth as well through a filling together with an embodiment of the tool according to this application in various operating positions, FIG. 2 shows a partial cross-section through a tooth as well through a filling, together with the tool according to FIG. 1, however, in a position different from that shown in FIG. 1, FIG. 3 shows the tool according to FIGS. 1 and 2 individually and in a lateral view.

Within the Figures a tooth 1 and a tooth filling 2, f.e. an amalgan filling, are shown; the filling 2 is treated or finished by means of the finisher 3, which comprises a rotation-symmetrical, conical body 4 with a rounded tip 5 and a base 6, which extends vertically to the symmetrical axis S of the conical body 4 and is opposite to the tip 5. The conical body 4 is provided with a plurality of cutting edges 7 on its surface, which edges extend in an inclined angle to the symmetrical axis.

A stem 8 extends from the base 6. This stem is formed in one piece with the conical body 4, f.e. from metal, preferably hard metal (carbide metal). The axis of the stem is coaxial with the symmetrical axis S. Stem 8 is used for connecting the finisher to a dental instrument and by means of this stem the finisher 3 is rotated around the axis S.

If the dental tool is a grinding and/or polishing tool the conical body 4 forms a grinding and/or polishing surface on its generated surface 7, and is provided on this surface with diamond chips or with a polishing material (abrasion material). The conical body 4 can be made of metal or any other suitable material, f.i. plastics. It is also possible to make the body 4 completely of polishing material or alternatively of material, which acts as a polisher.

With the described and shown embodiment according to this invention the diameter of the finisher at the base 6 is 1.5 until 1.7 units and the distance of the tip 5 from the base 6 is 3.5 units, whereby one unit f.e. corresponds to 1.0 mm. The surface line (or generatrix) 9 of the conical body is convexly curved over its entire length in such a manner that the diameter D varies dependent on the distance A as follows:

| A | D |
|---|---|
| 0 units | 1,5 until 1,7 units |
| 1 unit | 1,3 until 1,45 units |
| 2 units | 1,0 until 1,2 units |
| 3 units | 0,5 until 0,7 units. |

A special and preferred embodiment of the conical body has the following values:

| A | D |
|---|---|
| 0 units | 1,6 units |
| 1 unit | 1,45 units |
| 2 units | 1,15 units |
| 3 units | 0,6 units | whereby the radius of curvature at the tip 5 has a value corresponding to 0.2 units.

As shown within the Figures various operation steps can be performed with the finisher or alternatively with the grinding and/or polishing tool 3. In its position characterised by I in FIG. 1 the finisher 3 is used for finishing or levelling the filling 2 adjacent the transition of the filling 2 to tooth 1, in order to obtain an as continuous as possible transition to the surface 1' of the tooth by removing excessive material at the surfce 2' of the filling 2 (finishing the filling transitions). This finishing step of the transition of the filling is made by applying the finisher 3 to its generated surface 7.

Within position II the finisher is used in order to finish surface 2' of the filling within the area of the indentation corresponding to the natural shape of tooth 1. Tip 5 of the finisher 3 is used as the working surface (finishing of the fissures).

Using the finisher 3 according to FIG. 2 or alternatively according to position III excessive filling material 2'' is removed by means of the finisher, which material extends beyond the level required for the surface 2'. Considering the shape, which is to be obtained for surface 2' finisher 3 with this operation step initially mainly with the area of the finisher's generated surface close to the tip engages the excessive filling material 2'', and lateron also those areas of the finisher's generated surface, which are further away from the tip 5 will engage the filling material, as this is shown by an interrupted line within FIG. 2. During operation the finisher 3 is moved or alternatively turned, as well transverse to the symmetrical axis S as essentially vertical thereto, as is shown by arrows in FIG. 2.

A corresponding grinding or polishing tool 3 is used for working on the filling 3 adjacent to the transition to tooth 1. This is made by applying the tool 3 at its generated surface, whereby the tip 5 of the tool 3 is used as the operating surface. Using this tool according to FIG. 2 or alternatively according to position III is done as described above in connection with the finisher.

I claim:

1. A dental finisher tool, comprising a conical body having a base at one end and a rounded tip at its opposite end and having an outer surface in the form of a surface of rotation that is symmetrical with respect to the axis extending from said base to said rounded tip, said rounded tip and said outer surface providing the working surface of said tool, said conical body being rotatable about said axis of symmetry; a stem extending from said base and coaxial with said axis of symmetry; a plurality of cutting means on said outer surface of said conical body for finishing a tooth filling; the radius of curvature of said rounded tip being about 0.2 millimeters and said outer surface being convexly curved along the entire distance from said base to said rounded tip such that with said base having a diameter in the range of 1.5 to 1.7 millimeters and with the distance between said tip and said base being about 3.5 millimeters, the diameter of said conical body is a function of its distance from the base as follows:

| Distance From Base (millimeters) | Diameter (millimeters) |
|---|---|
| 1 [unit] | 1.3 to 1.45 [units] |
| 2 [units] | 1.0 to 1.2 [units] |
| 3 [units] | 0.5 to 0.7 [units] | whereby the user of the tool can work on multiple tooth surfaces, including fissures, with a single tool.

2. A dental tool according to claim 1, wherein the cutting means has cutting edges inclined with respect to said axis of symmetry.

3. A dental tool according to claim 1, wherein the base has a diameter of 1.6 millimeters, and wherein the diameter of the conical body is a function of its distance from the base as follows:

| Distance From Base (millimeters) | Diameter (millimeters) |
|---|---|
| 1 | 1.45 |
| 2 | 1.15 |
| 3 | 0.6 |

4. A grinding and/or polishing dental tool, comprising a conical body having a base at one end and a rounded tip at its opposite end and having an outer surface in the form of a surface of rotation that is symmetrical with respect to the axis extending from said base to said rounded tip, said rounded tip and said outer surface providing the working surface of said tool, said conical body being rotatable about saix axis of symmetry; a stem extending from said base and coaxial with said axis of symmetry; grinding and/or polishing means on said outer surface for grinding and/or polishing a tooth filling; the radius of curvature of said rounded tip being about 0.2 millimeters and said outer surface being convexly curved along the entire distance from said base to said rounded tip such that with said base having a diameter in the range of 1.5 to 1.7 millimeters and with the distance between said tip and said base being about 3.5, millimeters, the diameter of said conical body is a function of its distance from the base as follows:

| Distance From Base (millimeters) | Diameter (millimeters) |
|---|---|
| 1 [unit] | 1.3 to 1.45 [units] |
| 2 [units] | 1.0 to 1.2 [units] |

-continued

| Distance From Base (millimeters) | Diameter (millimeters) |
| --- | --- |
| 3 [units] | 0.5 to 0.7 [units] | whereby the user of the tool can work on multiple tooth surfaces, including fissures, with a single tooth.

5. A dental tool according to claim 4, wherein the base has a diameter of 1.6, millimeters and wherein the diameter of the conical body is a function of its distance from the base as follows:

| Distance From Base (millimeters) | Diameter (millimeters) |
| --- | --- |
| 1 | 1.45 |
| 2 | 1.15 |
| 3 | 0.6 |

* * * * *